United States Patent
Zar et al.

(10) Patent No.: US 10,593,112 B1
(45) Date of Patent: Mar. 17, 2020

(54) CHAMBER RECONSTRUCTION FROM A PARTIAL VOLUME

(71) Applicant: Biosense Webster (Israel) Ltd., Yokneam (IL)

(72) Inventors: Lior Zar, Poria Illit (IL); Benjamin Cohen, Haifa (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/383,945

(22) Filed: Apr. 15, 2019

(51) Int. Cl.
   *G06T 17/20* (2006.01)
   *G16H 30/40* (2018.01)
   *G06T 15/08* (2011.01)

(52) U.S. Cl.
   CPC .............. *G06T 17/20* (2013.01); *G06T 15/08* (2013.01); *G16H 30/40* (2018.01); *G06T 2200/04* (2013.01)

(58) Field of Classification Search
   CPC .................................. G16H 30/40; G06T 15/08
   See application file for complete search history.

(56) References Cited

U.S. PATENT DOCUMENTS

| | | | |
|---|---|---|---|
| 6,169,817 B1 | 1/2001 | Parker et al. | |
| 7,937,136 B2 | 5/2011 | Harlev et al. | |
| 2003/0214289 A1* | 11/2003 | van Muiswinkel | ........................ G01R 33/56341 324/307 |
| 2006/0120591 A1 | 6/2006 | Cathier et al. | |
| 2007/0110294 A1* | 5/2007 | Schaap | .................... G06T 5/002 382/131 |
| 2011/0050692 A1* | 3/2011 | Zhang | .................... G06T 3/0093 345/424 |
| 2015/0018698 A1 | 1/2015 | Safran et al. | |
| 2015/0024337 A1* | 1/2015 | Blassnig | ................. G06T 15/06 433/29 |
| 2015/0164356 A1 | 6/2015 | Merschon et al. | |
| 2017/0221254 A1 | 8/2017 | Zar et al. | |

OTHER PUBLICATIONS

Lorensen, William E., and Cline, Harvey E., "Marching cubes: a high resolution 3D surface construction algorithm," ACM SIGGRAPH, 10 computer graphics, vol. 21, No. 4, ACM, 1987.

* cited by examiner

*Primary Examiner* — Edward Park
(74) *Attorney, Agent, or Firm* — Vincent J. Serrao

(57) ABSTRACT

A plurality of coordinates are mapped to respective first voxels. Each first voxel is assigned a value f(0), f(n) being a monotonic function defined between 0 and M inclusive. A plurality of second voxels $\{v_i\}$, each of which is at a distance $1 \leq d(v_i) \leq M$ voxels from a nearest first voxel, are assigned respective second values $\{f(d(v_i))\}$. Each of at least some of the second voxels is then iteratively assigned a weighted average of respective values of its immediate neighbors, any value differing from f(M) by not more than a first threshold being given a higher weight than any other value. A subset of the second voxels, each of which has a value differing from f(M) by more than a second threshold, are identified. Subsequently, a mesh representing a surface of a volume including the first voxels and the subset of the second voxels is generated.

20 Claims, 6 Drawing Sheets

CHAMBER RECONSTRUCTION FROM A PARTIAL VOLUME

FIELD OF THE INVENTION

The present invention is related to the field of computer modeling.

BACKGROUND

Some medical applications call for constructing a mesh model of an anatomical structure, such as a chamber of a heart.

Lorensen, William E., and Cline, Harvey E., "Marching cubes: a high resolution 3D surface construction algorithm," ACM SIGGRAPH computer graphics, Vol. 21, No. 4, ACM, 1987, which is incorporated herein by reference, presents an algorithm, called "Marching Cubes," that creates triangle models of constant density surfaces from 3D medical data.

SUMMARY OF THE INVENTION

There is provided, in accordance with some embodiments of the present invention, a system including a monitor and a processor. The processor is configured to map, to respective first voxels, respective coordinates of a plurality of locations within an anatomical cavity, and to assign, to each of the first voxels, a first value $f(0)$, $f(n)$ being a monotonic function defined for each integer n between 0 and M inclusive, M being a predefined positive integer. The processor is further configured to value a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$. The processor is further configured to iteratively revalue the second voxels, subsequently to valuing the second voxels, by iteratively assigning, to each voxel of at least some of the second voxels, a weighted average of respective values of immediate neighbors of the voxel, in which weighted average any one of the values differing from $f(M)$ by not more than a first predefined threshold $\Delta$ is given a higher weight than any other one of the values. The processor is further configured to identify a subset of the second voxels, subsequently to iteratively revaluing the second voxels, each of which subset has a value differing from $f(M)$ by more than a second predefined threshold. The processor is further configured to generate, by applying a mesh-generating algorithm to a volume that includes the first voxels and the subset of the second voxels, a mesh representing a surface of the volume, and to display the mesh on the monitor.

In some embodiments, the volume consists of the first voxels and the subset of the second voxels.

In some embodiments, the mesh-generating algorithm is a Marching Cubes algorithm.

In some embodiments, $f(n)$ is monotonically decreasing over a domain $[0, M]$.

In some embodiments, $f(M)=0$ and $f(M-1)=\Delta$.

In some embodiments, for any integer $n_0$ in a domain $[0, M-3]$, $f(n_0+1)$ is a predefined percentage of $f(n_0)$.

In some embodiments, the processor is configured to value the second voxels over M iterations, by, in each $j^{th}$ one of the iterations, valuing those of the second voxels for which $d(v_i)=j$.

In some embodiments, the processor is configured to value the second voxels using multiple parallel execution threads.

In some embodiments, the processor is configured to revalue the second voxels using multiple parallel execution threads.

There is further provided, in accordance with some embodiments of the present invention, a method that includes mapping, to respective first voxels, respective coordinates of a plurality of locations within an anatomical cavity, and assigning, to each of the first voxels, a first value $f(0)$, $f(n)$ being a monotonic function defined for each integer n between 0 and M inclusive, M being a predefined positive integer. The method further includes valuing a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$. The method further includes, subsequently to valuing the second voxels, iteratively revaluing the second voxels by iteratively assigning, to each voxel of at least some of the second voxels, a weighted average of respective values of immediate neighbors of the voxel, in which weighted average any one of the values differing from $f(M)$ by not more than a first predefined threshold $\Delta$ is given a higher weight than any other one of the values. The method further includes, subsequently to iteratively revaluing the second voxels, identifying a subset of the second voxels, each of which has a value differing from $f(M)$ by more than a second predefined threshold. The method further includes, by applying a mesh-generating algorithm to a volume that includes the first voxels and the subset of the second voxels, generating a mesh representing a surface of the volume.

In some embodiments, the anatomical cavity includes a chamber of a heart.

There is further provided, in accordance with some embodiments of the present invention, a computer software product including a tangible non-transitory computer-readable medium in which program instructions are stored. The instructions, when read by a processor, cause the processor to map, to respective first voxels, respective coordinates of a plurality of locations within an anatomical cavity, and to assign, to each of the first voxels, a first value $f(0)$, $f(n)$ being a monotonic function defined for each integer n between 0 and M inclusive, M being a predefined positive integer. The instructions further cause the processor to value a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$. The instructions further cause the processor to iteratively revalue the second voxels, subsequently to valuing the second voxels, by iteratively assigning, to each voxel of at least some of the second voxels, a weighted average of respective values of immediate neighbors of the voxel, in which weighted average any one of the values differing from $f(M)$ by not more than a first predefined threshold $\Delta$ is given a higher weight than any other one of the values. The instructions further cause the processor identify a subset of the second voxels, subsequently to iteratively revaluing the second voxels, each of which subset has a value differing from $f(M)$ by more than a second predefined threshold. The instructions further cause the processor to, by applying a mesh-generating algorithm to a volume that includes the first voxels and the subset of the second voxels, generate a mesh representing a surface of the volume.

The present invention will be more fully understood from the following detailed description of embodiments thereof, taken together with the drawings, in which:

DETAILED DESCRIPTION OF EMBODIMENTS

Overview

Figure 1:
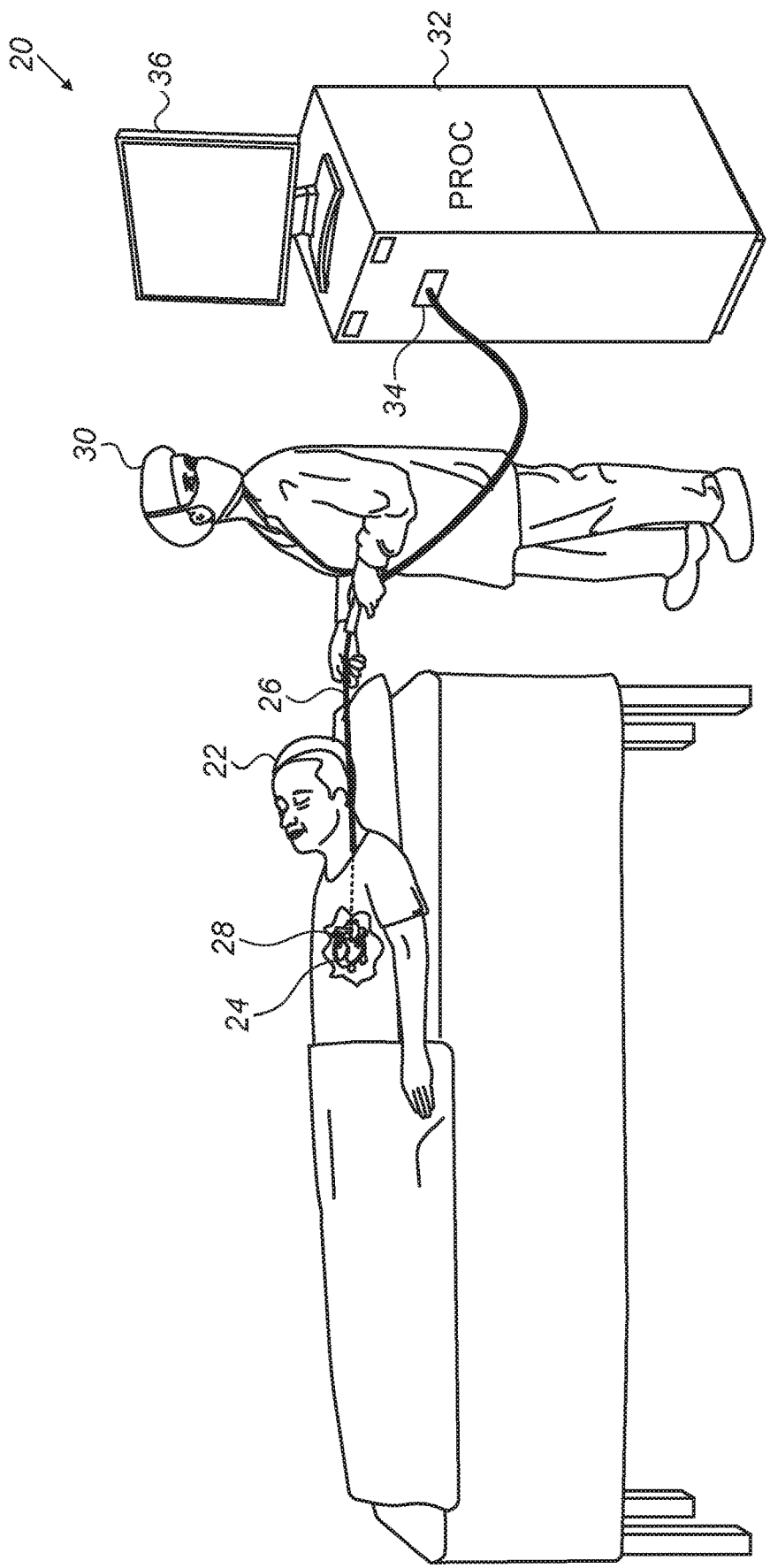
FIG. 1 is a schematic illustration of a system for generating a mesh model of one or more chambers of a heart of a subject, in accordance with some embodiments of the present invention.

Embodiments of the present invention provide a technique for constructing a mesh model (also referred to herein simply as a "mesh") of a chamber of a heart. Per this technique, while a catheter is moved within the chamber (and, optionally, within an adjoining blood vessel), the location of the catheter is continually recorded by a tracking system. Each of the recorded locations, or "points," is added to a "point cloud" representing the chamber. Subsequently, a volume of voxels is constructed from the point cloud, and the mesh is then constructed from the volume.

A particular challenge addressed by embodiments of the present invention is that gaps in the voxel volume may complicate the construction of the mesh. For example, the Marching Cubes algorithm, which is cited above in the Background, may consider the gaps to be external to the volume, and may hence tessellate the interior of the volume. Although other algorithms may be used to fill the gaps while constructing the mesh, these algorithms may be slow, and do not always handle all of the gaps effectively.

To address this challenge, embodiments of the present invention provide a processor configured to execute a filling algorithm for filling most or all of the gaps in the volume. By virtue of this filling, a fast and efficient mesh-construction algorithm, such as Marching Cubes, may be used to construct the mesh.

The filling algorithm operates on a neighborhood of the volume that includes (i) the set of original voxels derived from the point cloud, which are designated herein as $\{v_c\}$, and (ii) a set of other voxels $\{v_o\}$, each of which is at a distance of M or fewer voxels from the nearest voxel belonging to $\{v_c\}$. M is chosen to be sufficiently large such that each voxel representing a sub-volume of the chamber is at a distance of fewer than M voxels from the nearest voxel belonging to $\{v_c\}$.

When executing the filling algorithm, the processor first assigns a value of one to each voxel in $\{v_c\}$, and non-zero values to some of the voxels in $\{v_o\}$. In particular, the processor assigns a value $f(d(v_i))$ to each voxel $v_i$ in $\{v_o\}$, where $d(v_i)$ is the distance (in voxels) of $v_i$ from the nearest voxel in $\{v_c\}$, and $f(n)$ is a monotonically decreasing function of n over the domain [0, M] such that $f(0)=1$ and $f(M)=0$. Advantageously, this assignment of values may be performed on multiple parallel threads of execution (e.g., using a graphics processing unit (GPU)), in that the voxels belonging to $\{v_o\}$ may be valued in parallel to each other.

Next, the processor iteratively revalues the voxels in $\{v_o\}$ that are at a distance of less than M. In particular, in each iteration, each of these voxels is assigned a weighted average of the values of its immediate neighbors. In computing this weighted average, all non-zero values receive equal weighting, while each zero value receives a significantly larger weighting than the non-zero values. Thus, provided that the number of iterations is large enough, the processor nullifies all, or at least the vast majority of, the voxels representing sub-volumes that lie outside the chamber. (As noted above, M is generally large enough such that no voxels within the chamber are zero-valued, such that voxels within the chamber are not nullified.) Advantageously, this revaluing may also be performed on multiple parallel threads of execution.

Subsequently, the processor joins, to the volume, those of the voxels in $\{v_o\}$ having a value greater than a predefined threshold between zero and one. The processor thus fills the gaps in the volume.

Finally, the processor executes a fast mesh-generating algorithm, such as Marching Cubes, on the filled volume. The mesh may then be displayed on a computer screen. Optionally, the mesh may be overlaid with electrophysiological information, such as local activation time (LAT) values, so as to produce an electroanatomical map.

Although the present specification relates mainly to a chamber of a heart, it is noted that the techniques described herein may also be used to model any other anatomical or non-anatomical structure. For example, the techniques described herein may be used in depth-sensing applications.

System Description

Reference is initially made to FIG. 1, which is a schematic illustration of a system 20 for generating a mesh model of one or more chambers of a heart 24 of a subject 22, in accordance with some embodiments of the present invention.

FIG. 1 shows a physician 30 operating a catheter 26, a distal end 28 of which is disposed within heart 24. As physician 30 moves distal end 28 of catheter 26 within a chamber of the heart, the location of the distal end of the catheter is ascertained by a processor 32 belonging to system 20.

For example, the distal end of the catheter may comprise one or more electromagnetic sensors, which, in the presence of a generated magnetic field, output signals indicating the respective locations of the sensors. These signals may be received, via an electrical interface 34 (such as a port or socket), by processor 32. Based on the signals, processor 32 may ascertain the location of the distal end of the catheter.

Alternatively or additionally, the distal end of the catheter may comprise a catheter electrode, and a plurality of electrode patches may be coupled to the body of subject 22. As voltages are applied between the catheter electrode and the electrode patches, the respective magnitudes of the currents between the catheter electrode and the electrode patches may be measured. Based on these current magnitudes, the processor may ascertain the location of the distal end of the catheter. Alternatively or additionally, any other suitable technique may be used to track the distal end of the catheter.

In some embodiments, system 20 further comprises a monitor 36. As the physician operates catheter 26, processor 32 may superimpose, on monitor 36, an icon representing the distal end of the catheter over an image of the subject's heart, such that the physician may visually track the location of the distal end. Alternatively or additionally, following the generation of the mesh model (as described in detail hereinbelow), the processor may display the mesh model on monitor 36.

In general, processor 32 may be embodied as a single processor, or as a cooperatively networked or clustered set of processors. In some embodiments, the functionality of processor 32, as described herein, is implemented solely in hardware, e.g., using one or more Application-Specific Integrated Circuits (ASICs) or Field-Programmable Gate Arrays (FPGAs). In other embodiments, the functionality of processor 32 is implemented at least partly in software. For example, in some embodiments, processor 32 is a programmed digital computing device comprising a central processing unit (CPU), random access memory (RAM), non-volatile secondary storage, such as a hard drive or CD ROM drive, network interfaces, and/or peripheral devices. Optionally, processor 32 may further comprise a GPU. Program code, including software programs, and/or data are loaded into the RAM for execution and processing by the CPU and/or GPU, and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Notwithstanding the particular application shown in FIG. 1, it is noted that the mesh-generating techniques described herein may be used to model the surface of any structure. The structure may include any anatomical or non-anatomical cavity.

Mesh Generation

Figure 2:
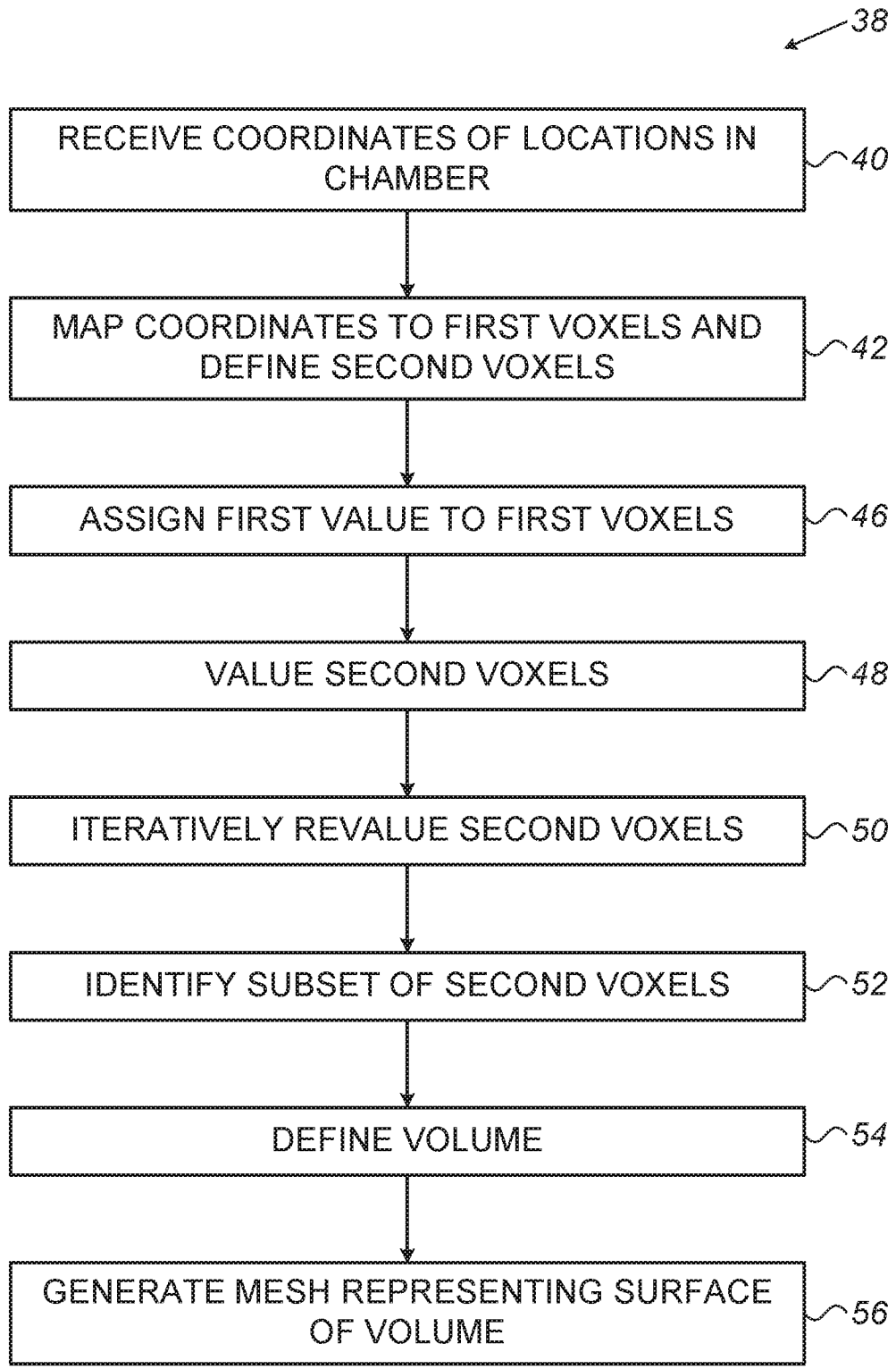
FIG. 2 is a flow diagram for a method for generating a mesh model, in accordance with some embodiments of the present invention.
Figure 3:
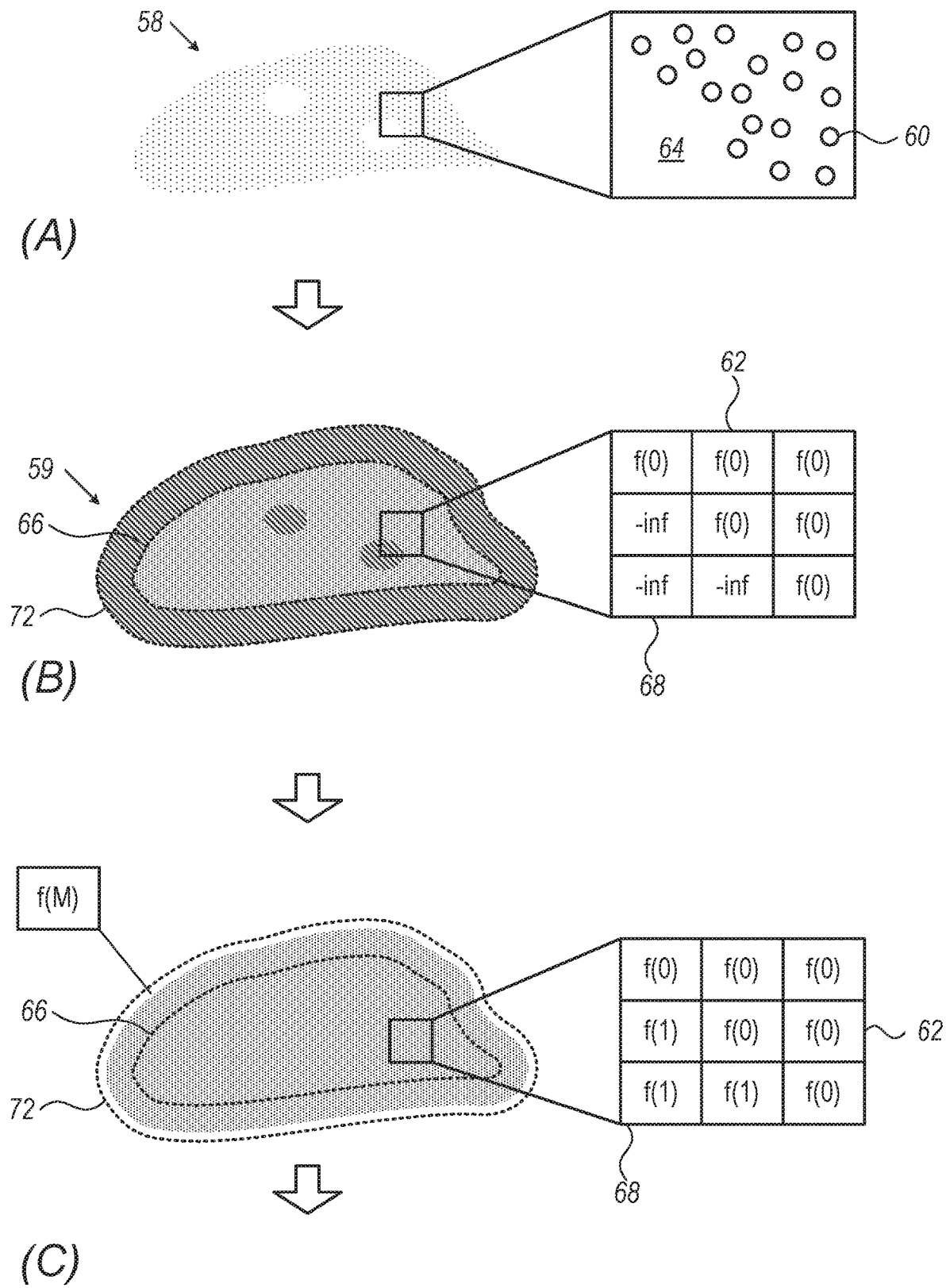
FIG. 3 is a schematic illustration of various aspects of the method of FIG. 2, in accordance with some embodiments of the present invention.
Figure 3:
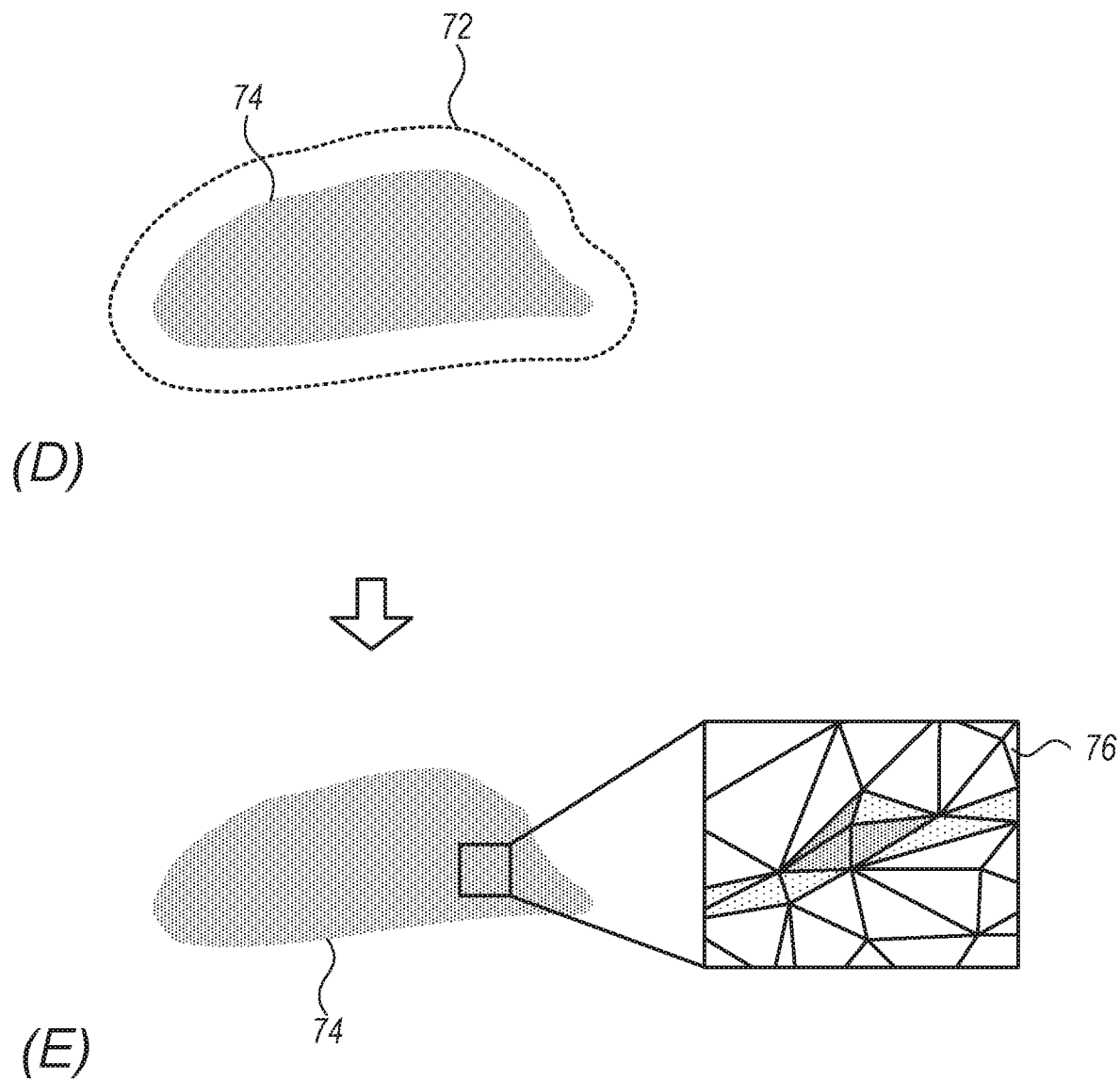

Reference is now made to FIG. 2, which is a flow diagram for a method 38 for generating a mesh model, which is performed by processor 32 in accordance with some embodiments of the present invention. Reference is further made to FIG. 3, which is a schematic illustration of various aspects of method 38, in accordance with some embodiments of the present invention. (For ease of illustration, the present drawings depict voxels as two-dimensional squares.)

Method 38 begins with a receiving step 40, at which the processor receives the respective coordinates 60 of a plurality of locations within a chamber of heart 24. For example, as described above with reference to FIG. 1, coordinates 60 may be received from a location-ascertaining routine, which ascertains the location of the distal end of catheter 26 as the distal end is moved within the chamber. Each coordinate 60 may also be referred to as a "point," and the collection of coordinates 60, shown in section A of FIG. 3, may be referred to as a "point cloud" 58. Point cloud 58 typically includes hundreds, thousands, or tens of thousands of points, along with gaps 64 in which no points are present.

Next, at a mapping step 42, the processor maps coordinates 60 to respective first voxels 62, such that each first voxel 62 represents a different respective sub-volume of the chamber in which at least one of coordinates 60 lies. The processor also defines a plurality of second voxels 68, each of which represents a different respective sub-volume of a gap 64 or of the exterior of the chamber. First voxels 62 and second voxels 68 collectively define a contiguous "voxel cloud" 59, which is shown in section B of FIG. 3. (Notwithstanding the particular example shown in FIG. 3, it is noted that voxel cloud 59 may have any suitable shape, such as a three-dimensional grid shape, e.g., a cubic shape.) The processor further assigns to each of first voxels 62, at an assigning step 46, a first value f(0), where f(n) is a function having the properties described below.

For example, the processor may divide a volume that incorporates point cloud 58 into a plurality of sub-volumes, each of which may have any suitable size, such as 0.8 mm×0.8 mm×0.8 mm. Each of the sub-volumes may then be represented by a respective voxel. Each voxel representing a sub-volume in which at least one of coordinates 60 lies may then be designated as a first voxel 62, and may be assigned the value f(0).

In section B of FIG. 3, first voxels 62, each of which lies within the boundary 66 of point cloud 58, are represented by a first pattern indicating that values to these voxels have been assigned. In contrast, second voxels 68, which, at this stage, have only a default "placeholder" value such as negative infinity ("−inf"), are represented by a second pattern. As shown in this section of the figure, some second voxels lie within boundary 66, while others lie between boundary 66 and the perimeter 72 of the voxel cloud.

In general, f(n) is a monotonic function defined for each integer n between 0 and M inclusive, M being a predefined positive integer. (In general, M may vary considerably between applications.) For example, f(n) may monotonically decrease over the domain [0, M]. Typically, in such embodiments, f(0) is one while f(M) is zero.

In some embodiments, for any integer $n_0$ in the domain [0, M−3], $f(n_0+1)$ is a predefined percentage of $f(n_0)$. For example, for embodiments in which f(n) monotonically decreases over [0, M], $f(n_0+1)$ may be equal to $p*f(n_0)$, where p is between 0.8 and 0.95, over the domain [0, M−3]. In some such embodiments, f(M−1) is equal to p*f(M−2). Thus, for example, for M=10, f(M)=0, and p=0.9, the values attained by f(n) on the domain [0, M] may be 1, 0.9, 0.81, 0.73, 0.66, 0.59, 0.53, 0.48, 0.43, 0.39, and 0. In other such embodiments, f(M−1) is equal to a small number A, such as any number less than or equal to 0.0001, while f(M)=0.

Subsequently to mapping step 42 and assigning step 46, the processor, at a valuing step 48, values (i.e., assigns respective values to) second voxels 68. In particular, the processor assigns, to each second voxel 68, the value f(d), where d is the distance of the second voxel (in voxels) from the nearest first voxel.

In some embodiments, second voxels 68 are valued over M iterations, by, in each $j^{th}$ iteration, valuing the second voxels for which d=j. In this regard, reference is now additionally made to FIG. 4, which is a schematic illustration of a technique for iteratively valuing second voxels 68, in accordance with some embodiments of the present invention.

Figure 4:
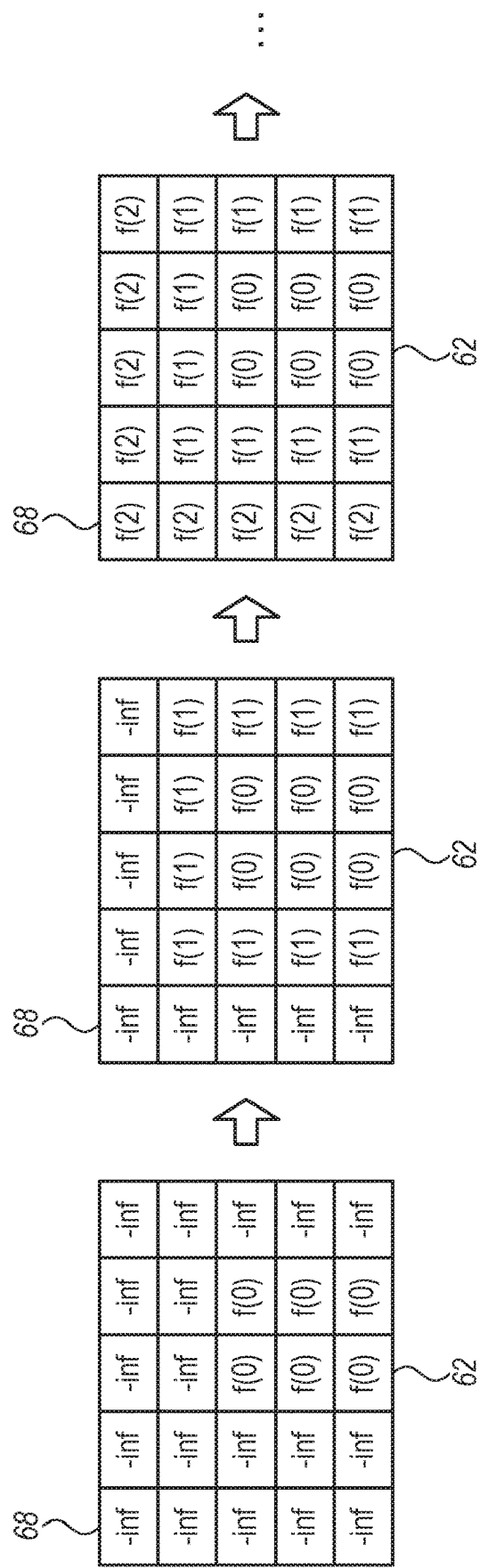
FIG. 4 is a schematic illustration of a technique for iteratively valuing voxels, in accordance with some embodiments of the present invention.

As shown in FIG. 4, during the first of the M iterations, a first subset of second voxels 68, each of which is an immediate neighbor of (i.e., is adjacent to) a first voxel 62, are assigned the value f(1). Similarly, during the second iteration, a second subset of the second voxels, each of which is an immediate neighbor of a member of the first subset, are assigned the value f(2). Each subsequent iteration then values another subset of the second voxels. (In practice, typically, during each $j^{th}$ iteration of the M iterations, all of the second voxels that have not yet been valued are processed. Those of the processed voxels having an immediate neighbor with the value f(j−1) are assigned the value f(j), while the others are not valued.)

In some embodiments, one voxel is said to be an immediate neighbor of (or "adjacent to") another voxel if the two voxels share at least one vertex. Thus, a voxel may have up to 26 immediate neighbors. (This criterion is assumed in FIG. 4, except that, due to the two-dimensional representation of the voxels, FIG. 4 shows eight, rather than 26, immediate neighbors.) In other embodiments, two voxels are said to be immediate neighbors of one another only if the two voxels share at least one face; thus, a voxel may have only up to six immediate neighbors. In yet other embodiments, yet other criteria may be used for determining the immediate neighbors of a voxel.

In some embodiments, second voxels 68 are valued using multiple parallel execution threads (running, for example, on a GPU). For example, during each of the M iterations, all of the second voxels that have not yet been valued may be processed in parallel.

The effect of valuing step 48 is shown in section C of FIG. 3, in which voxels near perimeter 72 are represented by white space, indicating that these voxels have been assigned the value f(M) (which in many embodiments, as noted above, is zero), while the remainder of the second voxels—including those that fill gaps 64—are represented by the first pattern, indicating that these voxels have been assigned other values. (Although section C does not show any unvalued second voxels, it is noted that, in practice, at least some voxels in voxel cloud 59 may be at a distance from the nearest first voxel that is greater than M, such that these voxels may remain unvalued (i.e., may remain with the default initial value). However, these voxels are not used in method 38.)

Following valuing step 48, the processor, at a revaluing step 50, performs a predefined number of iterations (e.g., between 100 and 200 iterations) through the second voxels. During each of these iterations, the processor revalues the second voxels, by assigning, to each voxel of at least some of the second voxels (typically, each of the second voxels that does not have a value of f(M)), a weighted average of respective values of immediate neighbors of the voxel. Typically, the weighted average gives a greater weight to any value that differs from f(M) by not more than a predefined threshold $\Delta$. (As noted above, in some embodiments, $f(M-1)=\Delta$ and $f(M)=0$.) For example, the weighted average may give an equal weight of one to all values that differ from f(M) by more than $\Delta$, while giving a weight of 40 or more, for example, to any value that differs from f(M) by $\Delta$ or less.

Figure 5A:
FIGS. 5A-B are schematic illustrations of a technique for iteratively revaluing voxels, in accordance with some embodiments of the present invention.
Figure 5B:

In this regard, reference is now additionally made to FIGS. 5A-B, which are schematic illustrations of a technique for iteratively revaluing second voxels 68, in accordance with some embodiments of the present invention. By way of illustration, each of these figures shows two revaluing iterations for a small representative collection of second voxels 68, ignoring any voxels that might lie outside of the collection. FIGS. 5A-B assume that f(M)=0 and that equal weight is given to all voxel values that are greater than $\Delta$. For convenience, in FIG. 5B, values that are not greater than $\Delta$ are written as 0.

The initial voxel values do not differ between FIGS. 5A-B, with only one exception: in FIG. 5B, one voxel 68a is zero-valued. Due to this one exception, however, the effect of the revaluing is markedly different in FIG. 5B. In particular, whereas, in FIG. 5A, the voxel values are "smoothed" across the collection of voxels, in FIG. 5B, the greater weight given to voxel 68a causes the entire collection to become zero-valued.

In general, provided that M is sufficiently large and that gaps 64 are not unusually large, the portion of voxel cloud 59 within boundary 66—representing the interior of the chamber—is smoothed, as in FIG. 5A, since this portion generally does not include f(M)-valued voxels. On the other hand, the portion of voxel cloud 59 outside boundary 66—representing the exterior of the chamber—is generally dominated by f(M), as in FIG. 5B, due to the presence of f(M)-valued voxels in this portion.

In some embodiments, the second voxels are revalued using multiple parallel execution threads, as described above for valuing step 48.

Subsequently to revaluing step 50, the processor, at a subset-identifying step 52, identifies a subset of the second voxels, each of which has a value differing from f(M) by more than another predefined threshold $\alpha$. For example, for embodiments in which f(M)=0, the processor may identify those second voxels whose values are greater than $\alpha$, where $\alpha$ is, for example, between 0.5 and 0.8. Subsequently, at a volume-defining step 54, and as shown in section D of FIG. 3, the processor defines a volume 74 that includes (typically, that consists of) first voxels 62 and the identified subset of the second voxels. In general, volume 74 includes most or all of the voxels within boundary 66, while excluding most or all of the voxels outside boundary 66.

Typically, the processor defines a table of values for voxel cloud 59. As assigning step 46, valuing step 48, and revaluing step 50 are executed, the processor updates the values in the table. Subsequently, at volume-defining step 54, the processor defines volume 74 by setting to f(0) those second voxels that differ from f(M) by more than $\alpha$, and setting the rest of the second voxels to f(M). Thus, for example, a value of one may be listed in the table for those voxels belonging to volume 74, while a value of zero may be listed for those voxels not belonging to volume 74.

Subsequently, at a mesh-generating step 56, the processor, by applying a mesh-generating algorithm to volume 74, generates a mesh 76, such as a triangular mesh, representing the surface of volume 74. Section E of FIG. 3 shows mesh 76, indicating the three-dimensional nature of the mesh by shading some of the triangles in the mesh.

In some embodiments, the processor uses the Marching Cubes algorithm to generate mesh 76. This algorithm generally requires, as input, a function defining the volume whose surface is to be tessellated. To satisfy this requirement, the processor may provide the aforementioned table of values, which indicates those voxels belonging to volume 74.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system, comprising:
a monitor; and
a processor, configured to:

map, to respective first voxels, respective coordinates of a plurality of locations within an anatomical cavity, assign, to each of the first voxels, a first value f(0),
f(n) being a monotonic function defined for each integer n between 0 and M inclusive, M being a predefined positive integer, value a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$, subsequently to valuing the second voxels, iteratively revalue the second voxels by iteratively assigning, to each voxel of at least some of the second voxels, a weighted average of respective values of immediate neighbors of the voxel,
in which weighted average any one of the values differing from f(M) by not more than a first predefined threshold $\Delta$ is given a higher weight than any other one of the values, subsequently to iteratively revaluing the second voxels, identify a subset of the second voxels, each of which has a value differing from f(M) by more than a second predefined threshold, by applying a mesh-generating algorithm to a volume that includes the first voxels and the subset of the second voxels, generate a mesh representing a surface of the volume, and display the mesh on the monitor.

2. The system according to claim 1, wherein the volume consists of the first voxels and the subset of the second voxels.

3. The system according to claim 1, wherein the mesh-generating algorithm is a Marching Cubes algorithm.

4. The system according to claim 1, wherein f(n) is monotonically decreasing over a domain [0, M].

5. The system according to claim 4, wherein f(M)=0 and f(M−1)=$\Delta$.

6. The system according to claim 1, wherein, for any integer $n_0$ in a domain [0, M−3], $f(n_0+1)$ is a predefined percentage of $f(n_0)$.

7. The system according to claim 1, wherein the processor is configured to value the second voxels over M iterations, by, in each $j^{th}$ one of the iterations, valuing those of the second voxels for which $d(v_i)=j$.

8. The system according to claim 7, wherein the processor is configured to value the second voxels using multiple parallel execution threads.

9. The system according to claim 1, wherein the processor is configured to revalue the second voxels using multiple parallel execution threads.

10. A method, comprising:
mapping, to respective first voxels, respective coordinates of a plurality of locations within an anatomical cavity;
assigning, to each of the first voxels, a first value f(0),
f(n) being a monotonic function defined for each integer n between 0 and M inclusive, M being a predefined positive integer;
valuing a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$;
subsequently to valuing the second voxels, iteratively revaluing the second voxels by iteratively assigning, to each voxel of at least some of the second voxels, a weighted average of respective values of immediate neighbors of the voxel,
in which weighted average any one of the values differing from f(M) by not more than a first predefined threshold $\Delta$ is given a higher weight than any other one of the values;

subsequently to iteratively revaluing the second voxels, identifying a subset of the second voxels, each of which has a value differing from f(M) by more than a second predefined threshold; and by applying a mesh-generating algorithm to a volume that includes the first voxels and the subset of the second voxels, generating a mesh representing a surface of the volume.

11. The method according to claim 10, wherein the volume consists of the first voxels and the subset of the second voxels.

12. The method according to claim 10, wherein the anatomical cavity includes a chamber of a heart.

13. The method according to claim 10, wherein the mesh-generating algorithm is a Marching Cubes algorithm.

14. The method according to claim 10, wherein f(n) is monotonically decreasing over a domain [0, M].

15. The method according to claim 14, wherein f(M)=0 and f(M−1)=$\Delta$.

16. The method according to claim 10, wherein, for any integer $n_0$ in a domain [0, M−3], $f(n_0+1)$ is a predefined percentage of $f(n_0)$.

17. The method according to claim 10, wherein valuing the second voxels comprises valuing the second voxels over M iterations, by, in each $j^{th}$ one of the iterations, valuing those of the second voxels for which $d(v_i)=j$.

18. The method according to claim 17, wherein valuing the second voxels comprises valuing the second voxels using multiple parallel execution threads.

19. The method according to claim 10, wherein revaluing the second voxels comprises revaluing the second voxels using multiple parallel execution threads.

20. A computer software product comprising a tangible non-transitory computer-readable medium in which program instructions are stored, which instructions, when read by a processor, cause the processor to:
map, to respective first voxels, respective coordinates of a plurality of locations within an anatomical cavity,
assign, to each of the first voxels, a first value f(0),
f(n) being a monotonic function defined for each integer n between 0 and M inclusive, M being a predefined positive integer,
value a plurality of second voxels $\{v_i\}$, each of which is at a distance $1 \leq d(v_i) \leq M$ voxels from a nearest one of the first voxels, by assigning, to the second voxels, respective second values $\{f(d(v_i))\}$,
subsequently to valuing the second voxels, iteratively revalue the second voxels by iteratively assigning, to each voxel of at least some of the second voxels, a weighted average of respective values of immediate neighbors of the voxel,
in which weighted average any one of the values differing from f(M) by not more than a first predefined threshold $\Delta$ is given a higher weight than any other one of the values,
subsequently to iteratively revaluing the second voxels, identify a subset of the second voxels, each of which has a value differing from f(M) by more than a second predefined threshold, and
by applying a mesh-generating algorithm to a volume that includes the first voxels and the subset of the second voxels, generate a mesh representing a surface of the volume.

* * * * *